(12) United States Patent
Fisher

(10) Patent No.: US 8,502,024 B2
(45) Date of Patent: Aug. 6, 2013

(54) SWEET CORN HYBRID SEY6RH1263 AND PARENTS THEREOF

(75) Inventor: David E. Fisher, Waunakee, WI (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 223 days.

(21) Appl. No.: 13/107,608

(22) Filed: May 13, 2011

(65) Prior Publication Data

US 2012/0291152 A1    Nov. 15, 2012

(51) Int. Cl.
*A01H 5/10* (2006.01)
*A01H 5/00* (2006.01)
*A01H 4/00* (2006.01)
*C12N 15/82* (2006.01)
*C12N 15/10* (2006.01)

(52) U.S. Cl.
USPC ........... 800/275; 800/260; 800/265; 800/266; 800/278; 800/320.1; 435/320.1; 435/468; 536/23.1

(58) Field of Classification Search
None
See application file for complete search history.

(56) References Cited

PUBLICATIONS

U.S. Appl. No. 13/107,755, Fisher.
Sep. 18, 2012 Information Disclosure Statement for U.S. Appl. No. 13/107,608.

*Primary Examiner* — Brent T Page
(74) *Attorney, Agent, or Firm* — Dentons US LLP; Alissa Eagle Esq.

(57) ABSTRACT

The invention provides seed and plants of sweet corn hybrid SEY6RH1263 and the parent lines thereof. The invention thus relates to the plants, seeds and tissue cultures of sweet corn hybrid SEY6RH1263 and the parent lines thereof, and to methods for producing a sweet corn plant produced by crossing such plants with themselves or with another sweet corn plant, such as a plant of another genotype. The invention further relates to seeds and plants produced by such crossing. The invention further relates to parts of such plants, including the parts of such plants.

27 Claims, No Drawings

SWEET CORN HYBRID SEY6RH1263 AND PARENTS THEREOF

FIELD OF THE INVENTION

The present invention relates to the field of plant breeding and, more specifically, to the development of sweet corn hybrid SEY6RH1263 and the inbred sweet corn lines SEY-6RNTB001 and SEY084-SESM1709.

BACKGROUND OF THE INVENTION

The goal of vegetable breeding is to combine various desirable traits in a single variety/hybrid. Such desirable traits may include any trait deemed beneficial by a grower and/or consumer, including greater yield, better stalks, better roots, resistance to insecticides, herbicides, pests, and disease, tolerance to heat and drought, reduced time to crop maturity, better agronomic quality, higher nutritional value, sugar content, uniformity in germination times, stand establishment, growth rate and maturity, among others.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a plant of the sweet corn hybrid designated SEY6RH1263, the sweet corn line SEY-6RNTB001 or sweet corn line SEY084-SESM1709. Also provided are corn plants having all the physiological and morphological characteristics of such a plant. Parts of these corn plants are also provided, for example, including pollen, an ovule, and a cell of the plant.

In another aspect of the invention, a plant of sweet corn hybrid SEY6RH1263 and/or sweet corn lines SEY-6RNTB001 and SEY084-SESM1709 comprising an added heritable trait is provided. The heritable trait may comprise a genetic locus that is, for example, a dominant or recessive allele. In one embodiment of the invention, a plant of sweet corn hybrid SEY6RH1263 and/or sweet corn lines SEY-6RNTB001 and SEY084-SESM1709 is defined as comprising a single locus conversion. In specific embodiments of the invention, an added genetic locus confers one or more traits such as, for example, male sterility, herbicide resistance, insect resistance, resistance to bacterial, fungal, sugar content, nematode or viral disease, and altered fatty acid, phytate or carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of sweet corn hybrid SEY6RH1263 and/or sweet corn lines SEY-6RNTB001 and SEY084-SESM1709. The corn seed of the invention may be provided, in one embodiment of the invention, as an essentially homogeneous population of corn seed of sweet corn hybrid SEY6RH1263 and/or sweet corn lines SEY-6RNTB001 and SEY084-SESM1709. Essentially homogeneous populations of seed are generally free from substantial numbers of other seed. Therefore, seed of hybrid SEY6RH1263 and/or sweet corn lines SEY-6RNTB001 and SEY084-SESM1709 may, in particular embodiments of the invention, be provided forming at least about 97% of the total seed, including at least about 98%, 99% or more of the seed. The seed population may be separately grown to provide an essentially homogeneous population of sweet corn plants designated SEY6RH1263 and/or sweet corn lines SEY-6RNTB001 and SEY084-SESM1709.

In yet another aspect of the invention, a tissue culture of regenerable cells of a sweet corn plant of hybrid SEY6RH1263 and/or sweet corn lines SEY-6RNTB001 and SEY084-SESM1709 is provided. The tissue culture will preferably be capable of regenerating corn plants capable of expressing all of the physiological and morphological characteristics of the starting plant, and of regenerating plants having substantially the same genotype as the starting plant. Examples of some of the physiological and morphological characteristics of the hybrid SEY6RH1263 and/or sweet corn lines SEY-6RNTB001 and SEY084-SESM1709 include those traits set forth in the tables herein. The regenerable cells in such tissue cultures may be derived, for example, from embryos, meristematic cells, immature tassels, microspores, pollen, leaves, anthers, roots, root tips, silk, flowers, kernels, ears, cobs, husks, or stalks, or from callus or protoplasts derived from those tissues. Still further, the present invention provides corn plants regenerated from a tissue culture of the invention, the plants having all the physiological and morphological characteristics of hybrid SEY6RH1263 and/or sweet corn lines SEY-6RNTB001 and SEY084-SESM1709.

In still yet another aspect of the invention, processes are provided for producing corn seeds, plants and parts thereof, which processes generally comprise crossing a first parent corn plant with a second parent corn plant, wherein at least one of the first or second parent corn plants is a plant of sweet corn line SEY-6RNTB001 or sweet corn line SEY084-SESM1709. These processes may be further exemplified as processes for preparing hybrid corn seed or plants, wherein a first corn plant is crossed with a second corn plant of a different, distinct genotype to provide a hybrid that has, as one of its parents, a plant of sweet corn line SEY-6RNTB001 or sweet corn line SEY084-SESM1709. In these processes, crossing will result in the production of seed. The seed production occurs regardless of whether the seed is collected or not.

In one embodiment of the invention, the first step in "crossing" comprises planting seeds of a first and second parent corn plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent corn plants into plants that bear flowers. A third step may comprise preventing self-pollination of the plants, such as by emasculating the flowers (i.e., killing or removing the pollen).

A fourth step for a hybrid cross may comprise cross-pollination between the first and second parent corn plants. Yet another step comprises harvesting the seeds from at least one of the parent corn plants. The harvested seed can be grown to produce a corn plant or hybrid corn plant.

The present invention also provides the corn seeds and plants produced by a process that comprises crossing a first parent corn plant with a second parent corn plant, wherein at least one of the first or second parent corn plants is a plant of sweet corn hybrid SEY6RH1263 and/or sweet corn lines SEY-6RNTB001 and SEY084-SESM1709. In one embodiment of the invention, corn seed and plants produced by the process are first generation ($F_1$) hybrid corn seed and plants produced by crossing a plant in accordance with the invention with another, distinct plant. The present invention further contemplates plant parts of such an $F_1$ hybrid corn plant, and methods of use thereof. Therefore, certain exemplary embodiments of the invention provide an $F_1$ hybrid corn plant and seed thereof.

In still yet another aspect, the present invention provides a method of producing a plant derived from hybrid SEY6RH1263 and/or sweet corn lines SEY-6RNTB001 and SEY084-SESM1709, the method comprising the steps of: (a) preparing a progeny plant derived from hybrid SEY6RH1263 and/or sweet corn lines SEY-6RNTB001 and SEY084-SESM1709, wherein said preparing comprises crossing a plant of the hybrid SEY6RH1263 and/or sweet corn lines SEY-6RNTB001 and SEY084-SESM1709 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid SEY6RH1263 and/or sweet corn lines SEY-6RNTB001 and SEY084-SESM1709. The plant derived from hybrid SEY6RH1263 and/or sweet corn lines SEY-6RNTB001 and SEY084-SESM1709 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid SEY6RH1263 and/or sweet corn lines SEY-6RNTB001 and SEY084-SESM1709 is obtained which possesses some of the desirable traits of the line/hybrid as well as potentially other selected traits.

In certain embodiments, the present invention provides a method of producing food or feed comprising: (a) obtaining a plant of sweet corn hybrid SEY6RH1263 and/or sweet corn lines SEY-6RNTB001 and SEY084-SESM1709, wherein the plant has been cultivated to maturity, and (b) collecting at least one corn from the plant.

In still yet another aspect of the invention, the genetic complement of sweet corn hybrid SEY6RH1263 and/or sweet corn lines SEY-6RNTB001 and SEY084-SESM1709 is provided. The phrase "genetic complement" is used to refer to the aggregate of nucleotide sequences, the expression of which sequences defines the phenotype of, in the present case, a sweet corn plant, or a cell or tissue of that plant. A genetic complement thus represents the genetic makeup of a cell, tissue or plant, and a hybrid genetic complement represents the genetic make up of a hybrid cell, tissue or plant. The invention thus provides corn plant cells that have a genetic complement in accordance with the corn plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid SEY6RH1263 and/or sweet corn lines SEY-6RNTB001 and SEY084-SESM1709 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by corn plant cells, tissues, plants, and seeds, formed by the combination of a haploid genetic complement of a corn plant of the invention with a haploid genetic complement of a second corn plant, preferably, another, distinct corn plant. In another aspect, the present invention provides a corn plant regenerated from a tissue culture that comprises a hybrid genetic complement of this invention.

In still yet another aspect, the invention provides a method of determining the genotype of a plant of sweet corn hybrid SEY6RH1263 and/or sweet corn lines SEY-6RNTB001 and SEY084-SESM1709 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended.

For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of sweet corn hybrid SEY6RH1263, sweet corn line SEY-6RNTB001 and sweet corn line SEY084-SESM1709. The hybrid SEY6RH1263 was produced by the cross of parent lines SEY-6RNTB001 and SEY084-SESM1709. The parent lines show uniformity and stability within the limits of environmental influence. By crossing the parent lines, uniform seed hybrid SEY6RH1263 can be obtained.

SEY6RH1263 is a yellow sugary sweet corn hybrid. The hybrid is an early maturity variety taking about 1090 heat units from planting to mid-silk. The hybrid has shown high yield and recovery relative to other processing sweet corn hybrids of similar maturity.

The development of sweet corn hybrid SEY6RH1263 and its parent lines is summarized below.

A. Origin and Breeding History of Sweet Corn Hybrid SEY6RH1263

The hybrid SEY6RH1263 was produced from a cross of the lines designated SEY-6RNTB001 and SEY084-SESM1709. The parent lines are uniform and stable, as is a hybrid therefrom. A small percentage of variants can occur within commercially acceptable limits for almost any characteristic during the course of repeated multiplication. However no variants are expected.

SEY-6RNTB001 is a yellow sweet corn inbred which was selected for good eating quality, good ear size, and for having the RpG gene that provides resistance to some races of *Puccinia polysora* (common rust).

The development of parent line SEY-6RNTB001 can be summarized as follows:

Winter 1999-2000: The inbred line AS403 (a proprietary Seminis inbred) was grown in a Hawaii nursery on Molokai and was crossed to a stock carrying the RpG allele. This stock was obtained from Dr. Jerald Pataky of the University of Illinois. It was coded Seminis accession B142 and was an R168 field corn inbred converted to carry the RpG allele. This allele was reported by Dr. Art Hooker to have come from PI 163558. AS403 was grown in Hawaii nursery row 9803 and B142 was grown in nursery row 9764. The nursery was grown by Hawaiian Research Ltd. under a contract with Seminis.

Summer 2000: The second ear selection of the F1 of AS403 X B142 was grown in the Seminis DeForest, Wis. nursery in row 4198 and was cross pollinated with AS403 in nursery row 4197 to make a BC1.

Winter 2000-2001: The first ear selection of the BC1 (AS403 X B142 X AS403) was grown in the Seminis nursery at Melipilla, Chile in row 7580 and was cross pollinated with AS403 in nursery row 7579 to make a BC2.

Summer 2001: Inbred 351 (a proprietary Seminis inbred now named SEY093-351 under the Monsanto naming) was grown in Seminis DeForest, Wis. nursery in row 4366. This inbred was crossed with a rust resistant plant from the $9^{th}$ ear selection of the BC2 {[(AS403 X B 142) X AS403] X AS403} grown in row 3847.

Winter 2001-2002: The above cross with inbred 351 was grown in the Seminis Melipilla, Chile nursery in row 6818 and a rust resistant plant in row 6818 was cross pollinated with inbred 351 in row 6817 to make a BC1 to inbred 351.

Summer 2002: The $2^{nd}$ ear selection of the BC1 to inbred 351 was grown in the Seminis DeForest, Wis. nursery in row 5185 and a rust resistant plant in row 5185 was crossed with inbred 351 in row 5183 to make a BC2 to inbred 351.

Winter 2002-2003: The BC2 to inbred 351 was grown in the Seminis Melipilla, Chile nursery in row 8173 and self pollinated to give F2 ears.

Summer 2003: F2 seed of the ear 1 selection was grown Seminis DeForest, Wis. nursery row 5175 and rust resistant plants were pollinated.

Winter 2003-2004: F3 seed of the ear 1 selection was grown in Seminis Melipilla, Chile nursery row 4979 and self pollinated.

Summer 2004: F4 seed of the ear 1 selection was grown in Seminis DeForest, Wis. nursery row 3968 and rust resistant plants were self pollinated.

Winter 2004-2005: F5 seed of the ear 1 selection was grown in Seminis Melipilla, Chile nursery row 8502 and self pollinated.

Summer 2005: F6 seed of the $2^{nd}$ ear selection was grown in Seminis DeForest, Wis. nursery row 5859 and self pollinated. Ear 1 was selected and given the name designation SEY-6RNTB001.

Corn inbred SEY-6RNTB001 was named at the BC2F7 generation. This inbred was reproduced by self pollination in 2009-2010 in Melipilla, Chile winter nursery and judged to be stable. Fifty ear selections from the 2009 Chile increase were sent to Foundation Seed as Breeder's Seed. Inbred SEY-6RNTB001 is uniform for all traits observed.

SEY084-SESM1709 is an early yellow sweet corn inbred which was selected for good eating quality, resistance to Maize Dwarf Mosaic Virus (MDMV), Sugarcane Mosaic Virus (SCMV) and the Rp1D gene which provides resistance to some races of *Puccinia sorghi* (common rust).

The development of parent line SEY084-SESM1709 can be summarized as follows:

Summer 1996: The inbred line SEPN 2 (a proprietary Seminis inbred) was grown in the DeForest, Wis. nursery in row 3644 and was crossed by a plant in row 4321 of the nursery which had shown MDMV resistance and which carried the Rp1D gene. This stock in row 4321 was an S3 line but testing vs MDMV and common rust had shown it homozygous resistant to both pathogens. This F1 cross was given a source of N96: 3644×4321/1

Winter 1997-1998: The F1 was grown in Homestead, Fla. nursery row 228 and was cross pollinated with SEPN 2 (a proprietary Seminis inbred) in nursery row 227 to make a BC1. The nursery was grown for Seminis by 27 Farms who were paid for their services. The BC1 cross was given a source of C97: 228×227/1.

Summer 1997: The BC1 was grown in the Seminis DeForest, Wis. nursery in row 3761. Plants in the row were inoculated with Sugarcane Mosaic Virus (SCMV) and with *Puccinia sorghi*. Some of the plants resistant to both pathogens were selfed. The ear harvested from one of these plants was given the source designation N97: 3761/1*.

Winter 1997-1998: S1 seed of N97: 3761/1* was grown in Rancagua, Chile row 6208 and selfs were made. The Rancagua nursery was grown for Seminis by Massai Agricultural Services who were paid for their services. One of the S2 ears harvested was given the source designation E98: 6208/1*.

Summer 1998: S2 seed of E98: 6208/1* was grown ear-to-row in the Seminis Deforest, Wis. nursery in row 5314. Plants in the row were inoculated with SCMV and *Puccinia sorghi*. A plant resistant to both pathogens was self pollinated. The S3 ear harvested form that plant was given the source designation N98: 5314/1*.

Winter 1998-1999: S3 seed of N98: 5314/1* was grown ear-to-row in Hawaii nursery row 8588. Some of the plants in row 8588 were self pollinated. The nursery was grown for Seminis by Hawaiian Research Ltd. Who were paid for their services. One of the selfed ears harvested from row 8588 was given the source designation H99: 8588/1*.

Summer 1999: S4 seed of H99: 8588/1* was grown ear-to-row in DeForest, Wis. nursery in row 4240. Plants in the row were inoculated with Sugarcane Mosaic Virus (SCMV) and with *Puccinia sorghi*. All 17 plants in the row were resistant to MDMV but not all plants were resistant to *Puccinia sorghi*. Some of the plants resistant to both pathogens were selfed. The ear harvested from one of these plants was given the source designation N99: 4240/1*.

Winter 1999-2000: S5 seed of N99: 4240/1* was grown ear-to-row in row 7053 of the Seminis Melipilla, Chile nursery. Some plants were self pollinated. One of the selfed ears harvested from row 7053 was given the source designation E00: 7053/1*. This ear was also given the name designation N1195EQ9.

Summer 2000: S6 seed of E00: 7053/1* was grown ear-to-row in DeForest, Wis. nursery in row 3430. Plants in the row were inoculated with Sugarcane Mosaic Virus (SCMV) and with *Puccinia sorghi*. All 20 plants in the row were resistant to MDMV and were resistant to *Puccinia sorghi* race 0. Some of the plants were selfed. The ear harvested from one of these plants was given the source designation N00: 3430/1*.

Winter 2000-2001: S7 seed of N00: 3430/1* was grown ear-to-row in row 7988 of the Seminis Melipilla, Chile nursery. Some plants were self pollinated. Eight of the selfed ears were harvested and shelled seed from those ears was bulked into a single bag of seed. This bulk was given the source designation E01: 7988/B1*

Summer 2001: S8 seed of E01: 7988/B1* was grown ear-to-row in row 7146 of the Seminis Nampa, Id. nursery. All plants were observed for uniformity and self pollinated. All self pollinated ears were harvested and shelled seed from those ears was bulked into a single bag of seed. This bulk was given the source designation A01: 7146/*. This stock was given the name SESM1709. Later when Seminis naming policy changed the line was renamed SEY084-SESM1709.

Summer 2002: S9 seed of A01: 7146/* was grown in row 5057 of the Seminis Nampa, Id. nursery. All plants were observed for uniformity and self pollinated. All self pollinated ears were harvested and shelled seed from those ears was bulked into a single bag of seed. This bulk was given the source designation A02: 50571*.

Summer 2004: S10 seed of A02: 50571* was grown in row 9049 of the Seminis Nampa, Id. nursery. All plants were observed for uniformity and self pollinated. One of the pollinated ears was given a source designation of A04: 9049/12*.

Winter 2004-2005: S11 seed of A04: 9049/12* was planted in the DeForest, Wis. greenhouse experiment 2004-6 and all plants were inoculated with both SCMV and *Puccinia sorghi* race 0. All 38 plants tested were resistant to both pathogens. Seed of A04: 9049/12* was also grown in row 6832 of the Melipilla, Chile nursery. Plants were observed for uniformity and uniform ears were selected at harvest. All seed saved from this row was bulked as the first Foundation Seed increase for this inbred. This seed was given the source designation FSCC6382/05.

Corn inbred SEY084-SESM1709 was named at the BC1S9 generation. This inbred was reproduced at the BC1S11 by self pollination in the Winter 2004-2005 Melipilla, Chile winter nursery and judged to be stable. A bulk of ear selections from the 2004-2005 Chile increase made up the first Foundation Seed lot. Inbred SEY084-SESM1709 is uniform for all traits observed.

B. Physiological and Morphological Characteristics of Sweet Corn Hybrid SEY6RH1263, Sweet Corn Line SEY-6RNTB001 and Sweet Corn Line SEY084-SESM1709

In accordance with one aspect of the present invention, there is provided a plant having the physiological and morphological characteristics of sweet corn hybrid SEY6RH1263 and the parent lines thereof. A description of the physiological and morphological characteristics of such plants is presented in Tables 1-3.

TABLE 1

Physiological and Morphological Characteristics of Hybrid SEY6RH1263

| Characteristic | SEY6RH1263 | Comparison Variety-GH 2042 |
|---|---|---|
| 1. Type | sweet | sweet |
| 2. Region where developed in the U.S.A. | midwest | midwest |
| 3. Leaf | | |
| foliage: intensity of green color | medium | medium |
| first leaf: anthocyanin coloration of sheath | absent or very weak | medium |
| first leaf: shape of apex | pointed | pointed |
| leaf: undulation of margin of blade | absent or very weak | intermediate |
| leaf: angle between blade and stem (on leaf just above upper ear) | small (±25°) | very small |
| leaf: curvature of blade | slightly recurved | moderately recurved |
| leaf: anthocyanin coloration of sheath | absent or very weak | absent or very weak |
| leaf: width of blade | wide | medium |
| width of ear node leaf | 8.8 cm | 8.43 cm |
| | standard deviation: | standard deviation: |

TABLE 1-continued

Physiological and Morphological Characteristics of Hybrid SEY6RH1263

| Characteristic | SEY6RH1263 | Comparison Variety-GH 2042 |
|---|---|---|
| | 0.35051 | 0.7286 |
| | sample size: 15 | sample size: 15 |
| length of ear node leaf in centimeters | 72.36 cm<br>standard deviation: 2.3335<br>sample size: 15 | 79.33 cm<br>standard deviation: 3.3946<br>sample size: 15 |
| number of leaves above top ear | 5.2<br>standard deviation: 0.5606<br>sample size: 15 | 4.6<br>standard deviation 0.5071<br>sample size: 15 |
| degrees leaf angle | 40° | 40° |
| color | 5GY 4/4 | 5GY 4/4 |
| sheath pubescence (1 = none to 9 = like peach fuzz) | 9 | 8 |
| marginal waves (1 = none to 9 = many) | 1 | 7 |
| longitudinal creases (1 = none to 9 = many) | 8 | 6 |
| stem: degree of zig-zag | absent or very slight | slight |
| stem: anthocyanin coloration of brace roots | absent or very weak | absent or very weak |
| stem: anthocyanin coloration of internodes | absent or very weak | absent or very weak |

4. Plant

| Characteristic | SEY6RH1263 | Comparison Variety-GH 2042 |
|---|---|---|
| length (tassel included) (only inbred lines and varieties with ear type of grain: sweet or pop) | medium | long |
| ratio height of insertion of peduncle of upper ear to plant length | small | large |
| peduncle: length | short | long |
| plant height (to tassel tip) | 118.6 cm<br>standard deviation: 7.2806<br>sample size: 15 | 121.33 cm<br>standard deviation 8.7723<br>sample size: 30 |
| ear height (to base of top ear node) | 29.3 cm<br>standard deviation: 3.3209<br>sample size: 15 | 34.26 cm<br>standard deviation 7.6107<br>sample size: 15 |
| length of top ear internode | 12.94 cm<br>standard deviation: 1.3201<br>sample size: 15 | 18.03 cm<br>standard deviation: 2.5471<br>sample size: 15 |
| average number of tillers | 3.2 avg<br>standard deviation: 0.7745<br>sample size: 15 | 2.1 avg<br>standard deviation 0.4577<br>sample size: 15 |
| average number of ears per stalk | 1.8 avg<br>standard deviation: 0.41403<br>sample size: 15 | 1.6 avg<br>standard deviation: 0.5071<br>sample size: 15 |
| anthocyanin of brace roots | absent | absent |

5. Tassel

| Characteristic | SEY6RH1263 | Comparison Variety-GH 2042 |
|---|---|---|
| time of anthesis | very early | early |
| anthocyanin coloration at base of glume | absent or very weak | absent or very weak |
| anthocyanin coloration of glumes excluding base | absent or very weak | absent or very weak |
| anthocyanin coloration of anthers | absent or very weak | absent or very weak |
| angle between main axis and lateral branches | small (±25°) | small |
| curvature of lateral branches | absent or very slightly recurved | absent or very slightly recurved |
| number of primary lateral branches | many | few |
| density of spikelets | moderately dense | medium |
| length of main axis above lowest lateral branch (A-B) | medium | long |
| length of main axis above highest lateral branch (C-D) | medium | medium |
| length of lateral branch | short | medium |
| number of primary lateral | 33.93 | 24.1 |

TABLE 1-continued

Physiological and Morphological Characteristics of Hybrid SEY6RH1263

| Characteristic | SEY6RH1263 | Comparison Variety-GH 2042 |
|---|---|---|
| branches | standard deviation: 4.4315<br>sample size: 15 | standard deviation: 4.7278<br>sample size: 15 |
| branch angle from central spike | 27.66°<br>standard deviation: 10.9978<br>sample size: 15 | 41°<br>standard deviation: 8.981<br>sample size: 15 |
| length (from top leaf collar to tassel tip) | 34.33 cm<br>standard deviation: 2.0845<br>sample size: 15 | 37.23 cm<br>standard deviation: 2.7894<br>sample size: 15 |
| pollen shed (0 = male sterile to 9 = heavy shed) | 9 | 7 |
| anther color | 2.5R 7/4 | 2.5GY 7/4 |
| glume color | 2.5GY 8/2 | 5GY 7/4 |
| bar glumes (glume bands) | present | absent |
| 6. Ear | | |
| (unhusked data) silk color | 2.5GY 8/6 | 2.5GY 8/4 |
| (unhusked data) fresh husk color | 5GY 7/4 | 5GY 6/6 |
| (unhusked data) dry husk color | 2.5Y 8/6 | 2.5Y 8/4 |
| (unhusked data) position of ear at dry husk stage | horizontal | horizontal |
| (unhusked data) husk tightness (1 = very loose to 9 = very tight) | 2 | 5 |
| (unhusked data) husk extension (at harvest) | short (ears exposed) | medium |
| (husked ear data) ear length | 17.8 cm<br>standard deviation: 2.2819<br>sample size: 15 | 17.66 cm<br>standard deviation: 1.3047<br>sample size: 15 |
| (husked ear data) ear diameter at mid-point | 50.3 mm<br>standard deviation: 9.1255<br>sample size: 15 | 43.7 mm<br>standard deviation: 1.4959<br>sample size: 15 |
| (husked ear data) ear weight | 162.3 gm<br>standard deviation: 24.5754<br>sample size: 15 | 132 gm<br>standard deviation: 16.8607<br>sample size: 15 |
| (husked ear data) number of kernel rows | 20.2<br>standard deviation: 2.2103<br>sample size: 15 | 17.4<br>standard deviation: 1.4041<br>sample size: 15 |
| (husked ear data) kernel rows | indistinct | distinct |
| (husked ear data) row alignment | straight | slightly curved |
| (husked ear data) shank length | 15.2 cm<br>standard deviation: 2.6846<br>sample size: 15 | 16.4 cm<br>standard deviation: 4.8309<br>sample size: 15 |
| (husked ear data) ear taper | slight | distinct |
| length | long | long |
| diameter (in middle) | large | large |
| shape | conico-cylindrical | conico-cylindrical |
| number of rows of grain | medium | medium |
| number of colors of grains | one | one |
| (only varieties with ear type of grain: sweet or waxy) grain: intensity of yellow color (only varieties with ear type of grain: sweet) | medium | dark |
| grain: length (only varieties with ear type of grain: sweet) | long | long |
| grain: width (only varieties with ear type of grain: sweet) | broad | medium |
| type of grain | sweet | sweet |
| shrinkage of top of grain (only varieties with ear type of grain: sweet) | strong | medium |
| color of top of grain | yellow | yellow |
| anthocyanin coloration of glumes of cob | absent or very weak | absent or very weak |
| time of silk emergence (50% | very early | early |

TABLE 1-continued

Physiological and Morphological Characteristics of Hybrid SEY6RH1263

| Characteristic | SEY6RH1263 | Comparison Variety-GH 2042 |
|---|---|---|
| of plants) | | |
| anthocyanin coloration of silks | absent or very weak | absent or very weak |
| 7. Cob | | |
| diameter of mid-point | 28.1 mm<br>standard deviation: 2.7117<br>sample size: 15 | 24.3 mm<br>standard deviation: 1.1139<br>sample size: 15 |
| color | 2.5Y 8/4 | 2.5Y 8/2 |
| 8. Kernel (dried) | | |
| length | 12.5 mm<br>standard deviation: 0.5637<br>sample size: 15 | 10.8 mm<br>standard deviation: 0.6453<br>sample size: 15 |
| width | 7.4 mm<br>standard deviation: 1.109<br>sample size: 15 | 6.8 mm<br>standard deviation: 0.9259<br>sample size: 15 |
| thickness | 3.2 mm<br>standard deviation: 0.5398<br>sample size: 15 | 2.9 mm<br>standard deviation 0.5767<br>sample size: 15 |
| % round kernels (shape grade) | sample size: 15 | sample size: 15 |
| aleurone color pattern | homozygous | homozygous |
| aleurone color | 2.5Y 8/10 | 2.5Y 8/10 |
| hard endosperm color | 2.5Y 8/10 | 2.5Y 8/10 |
| endosperm type | sweet (su1) | sweet |
| weight per 100 kernels (unsized sample) | 18 gm<br>sample size: 100 | 23 gm<br>sample size: 100 |
| 9. Agronomic Traits | | |
| stay green (at 65 days after anthesis) (from 1 = worst to 9 = excellent) | 3 | 3 |
| dropped ears (at 65 days after anthesis) | 26.60% | 50% |

*These are typical values. Values may vary due to environment. Other values that are substantially equivalent are also within the scope of the invention.

TABLE 2

Physiological and Morphological Characteristics of Sweet Corn Line SEY-6RNTB001

| Characteristic | SEY-6RNTB001 | Comparison Variety-WE 10 |
|---|---|---|
| 1. Type | sweet | sweet |
| 2. Region where developed in the U.S.A. | midwest | midwest |
| 3. Leaf | | |
| foliage: intensity of green color | medium | dark |
| first leaf: anthocyanin coloration of sheath | absent or very weak | absent or very weak |
| first leaf: shape of apex | pointed | pointed to round |
| leaf: undulation of margin of blade | intermediate | intermediate |
| leaf: angle between blade and stem (on leaf just above upper ear) | large (±75°) | small |
| leaf: curvature of blade | slightly recurved | strongly recurved |
| leaf: anthocyanin coloration of sheath | absent or very weak | absent or very weak |
| leaf: width of blade | medium | narrow |
| width of ear node leaf | 7.26 cm<br>standard deviation: 0.4169<br>sample size: 15 | 7.48 cm<br>standard deviation: 0.8067<br>sample size: 45 |
| length of ear node leaf in centimeters | 59.8 cm<br>standard deviation: 2.56904<br>sample size: 15 | 73.77 cm<br>standard deviation: 3.4635<br>sample size: 45 |
| number of leaves above top ear | 5.7<br>standard deviation: 0.7037<br>sample size: 15 | 6.24<br>standard deviation 0.7075<br>sample size: 45 |
| degrees leaf angle | 70° | 30.1° |
| color | 5GY 4/6 | 5GY 3/4 |

TABLE 2-continued

Physiological and Morphological Characteristics of Sweet Corn Line SEY-6RNTB001

| Characteristic | SEY-6RNTB001 | Comparison Variety-WE 10 |
|---|---|---|
| sheath pubescence (1 = none to 9 = like peach fuzz) | 9 | 5 |
| marginal waves (1 = none to 9 = many) | 5 | 6 |
| longitudinal creases (1 = none to 9 = many) | 2 | 0 |
| stem: degree of zig-zag | absent or very slight | absent or very slight |
| stem: anthocyanin coloration of brace roots | absent or very weak | absent or very weak |
| stem: anthocyanin coloration of internodes | absent or very weak | absent or very weak |
| 4. Plant | | |
| length (tassel included) (only inbred lines and varieties with ear type of grain: sweet or pop) | short | long |
| ratio height of insertion of peduncle of upper ear to plant length | small | medium |
| peduncle: length | short | long |
| plant height (to tassel tip) | 79 cm<br>standard deviation: 9.1651<br>sample size: 15 | 91.86 cm<br>standard deviation 7.4712<br>sample size: 45 |
| ear height (to base of top ear node) | 21.26 cm<br>standard deviation: 2.0571<br>sample size: 15 | 29.94 cm<br>standard deviation 3.2529<br>sample size: 45 |
| length of top ear internode | 8.1 cm<br>standard deviation: 0.7121<br>sample size: 15 | 11.6 cm<br>standard deviation: 1.8103<br>sample size: 45 |
| average number of ears per stalk | 1.4 avg<br>standard deviation: 0.5071<br>sample size: 15 | 1.46 avg<br>standard deviation: 0.5768<br>sample size: 45 |
| anthocyanin of brace roots | absent | absent |
| 5. Tassel | | |
| time of anthesis | early | early |
| anthocyanin coloration at base of glume | absent or very weak | absent or very weak |
| anthocyanin coloration of glumes excluding base | weak | absent or very weak |
| anthocyanin coloration of anthers | absent or very weak | absent or very weak |
| angle between main axis and lateral branches | very small (<5°) | very small |
| curvature of lateral branches | absent or very slightly recurved | straight |
| number of primary lateral branches | many | medium |
| density of spikelets | medium | medium |
| length of main axis above lowest lateral branch (A-B) | short | medium |
| length of main axis above highest lateral branch (C-D) | very short | short |
| length of lateral branch | short | medium |
| number of primary lateral branches | 20.5<br>standard deviation: 6.5559<br>sample size: 15 | 33.7<br>standard deviation: 3.9892<br>sample size: 45 |
| branch angle from central spike | 22.66°<br>standard deviation: 5.6273<br>sample size: 15 | 34.7°<br>standard deviation: 9.1999<br>sample size: 45 |
| length (from top leaf collar to tassel tip) | 19.86 cm<br>standard deviation: 1.7368<br>sample size: 15 | 29.78 cm<br>standard deviation: 3.1981<br>sample size: 45 |
| pollen shed (0 = male sterile to 9 = heavy shed) | 9 | 8 |
| anther color | 2.5Y 8/6 | 2.5GY 8/10 |
| glume color | 2.5GY 7/4 | 5GY 6/6 |
| bar glumes (glume bands) | present | absent |

TABLE 2-continued

Physiological and Morphological Characteristics of Sweet Corn Line SEY-6RNTB001

| Characteristic | SEY-6RNTB001 | Comparison Variety-WE 10 |
|---|---|---|
| 6. Ear | | |
| (unhusked data) silk color | 2.5GY 8/4 | 25GY 8/6 |
| (unhusked data) fresh husk color | 2.5GY 6/8 | 2.5GY 6/8 |
| (unhusked data) dry husk color | 5Y 8/4 | 2.5Y 8/4 |
| (unhusked data) position of ear at dry husk stage | horizontal | upright |
| (unhusked data) husk tightness (1 = very loose to 9 = very tight) | 3 | 6 |
| (unhusked data) husk extension (at harvest) | long (8-10 cm beyond the ear tip) | medium |
| (husked ear data) ear length | 13.4 cm<br>standard deviation: 1.1153<br>sample size: 15 | 15.1 cm<br>standard deviation: 2.0126<br>sample size: 45 |
| (husked ear data) ear diameter at mid-point | 38.1 mm<br>standard deviation: 5.6794<br>sample size: 15 | 37.02 mm<br>standard deviation: 4.4629<br>sample size: 45 |
| (husked ear data) ear weight | 37.6 gm<br>standard deviation: 12.6923<br>sample size: 15 | 76.8 gm<br>standard deviation: 26.3475<br>sample size: 45 |
| (husked ear data) number of kernel rows | 12<br>standard deviation: 2.9032<br>sample size: 15 | 15.8<br>standard deviation: 3.0608<br>sample size: 45 |
| (husked ear data) kernel rows | indistinct | distinct |
| (husked ear data) row alignment | straight | straight |
| (husked ear data) shank length | 9.8 cm<br>standard deviation: 2.4886<br>sample size: 15 | 11.14 cm<br>standard deviation: 3.0598<br>sample size: 45 |
| (husked ear data) ear taper | extreme | slight |
| length | medium | medium |
| diameter (in middle) | large | medium |
| shape | conico-cylindrical | conico-cylindrical |
| number of rows of grain | medium | medium |
| number of colors of grains (only varieties with ear type of grain: sweet or waxy) | one | one |
| grain: intensity of yellow color (only varieties with ear type of grain: sweet) | light | dark |
| grain: length (only varieties with ear type of grain: sweet) | medium | medium |
| grain: width (only varieties with ear type of grain: sweet) | broad | medium |
| type of grain | sweet | sweet |
| shrinkage of top of grain (only varieties with ear type of grain: sweet) | medium | medium |
| color of top of grain | yellow | yellow |
| anthocyanin coloration of glumes of cob | absent or very weak | absent |
| time of silk emergence (50% of plants) | early | late to very late |
| anthocyanin coloration of silks | absent or very weak | absent |
| 7. Cob | | |
| diameter of mid-point | 27.4 mm<br>standard deviation: 1.8798<br>sample size: 15 | 27.65 mm<br>standard deviation: 2.1848<br>sample size: 45 |
| color | 2.5Y 8/2 | 5Y 8/4 |
| 8. Kernel (dried) | | |
| length | 8.3 mm<br>standard deviation: 1.5668<br>sample size: 15 | 7.05 mm<br>standard deviation: 0.9999<br>sample size: 45 |
| width | 7.9 mm<br>standard deviation: | 6.75 mm<br>standard deviation: |

TABLE 2-continued

Physiological and Morphological Characteristics of Sweet Corn Line SEY-6RNTB001

| Characteristic | SEY-6RNTB001 | Comparison Variety-WE 10 |
|---|---|---|
| thickness | 1.4203<br>sample size: 15<br>2.5 mm<br>standard deviation:<br>0.6725<br>sample size: 15 | 0.8364<br>sample size: 45<br>5 mm<br>standard deviation<br>0.9935<br>sample size: 45 |
| % round kernels (shape grade) | sample size: 15 | sample size: 45 |
| aleurone color pattern | homozygous | homozygous |
| aleurone color | 5Y 8/10 | 2.5Y 8/10 |
| hard endosperm color | 5Y 8/10 | 2.5Y 8/10 |
| endosperm type | sweet (su1) | sweet |
| weight per 100 kernels (unsized sample) | 18 gm<br>sample size: 100 | 16.25 gm<br>sample size: 200 |
| 9. Agronomic Traits | | |
| stay green (at 65 days after anthesis) (from 1 = worst to 9 = excellent) | 1 | 7 |

*These are typical values. Values may vary due to environment. Other values that are substantially equivalent are also within the scope of the invention.

TABLE 3

Physiological and Morphological Characteristics of Sweet Corn Line SEY084-SESM1709

| Characteristic | SEY 084-SESM1709 | Comparison Variety - WE 10 |
|---|---|---|
| 1. Type | sweet | sweet |
| 2. Region where developed in the U.S.A. | midwest | midwest |
| 3. Leaf | | |
| foliage: intensity of green color | medium | dark |
| first leaf: anthocyanin coloration of sheath | medium | absent or very weak |
| first leaf: shape of apex | pointed | pointed to round |
| leaf: undulation of margin of blade | intermediate | intermediate |
| leaf: angle between blade and stem (on leaf just above upper ear) | small (±25°) | small |
| leaf: curvature of blade | slightly recurved | strongly recurved |
| leaf: anthocyanin coloration of sheath | weak | absent or very weak |
| leaf: width of blade | medium | narrow |
| width of ear node leaf | 8.5 cm<br>standard deviation:<br>0.9063<br>sample size: 15 | 7.48 cm<br>standard deviation:<br>0.8067<br>sample size: 45 |
| length of ear node leaf in centimeters | 57.4 cm<br>standard deviation:<br>3.6606<br>sample size: 15 | 73.77 cm<br>standard deviation:<br>3.4635<br>sample size: 45 |
| number of leaves above top ear | 4.6<br>standard deviation:<br>0.7367<br>sample size: 15 | 6.24<br>standard deviation<br>0.7075<br>sample size: 45 |
| degrees leaf angle | 52° | 30.1° |
| color | 5GY 4/6 | 5GY 3/4 |
| sheath pubescence (1 = none to 9 = like peach fuzz) | 9 | 5 |
| marginal waves (1 = none to 9 = many) | 7 | 6 |
| longitudinal creases (1 = none to 9 = many) | 1 | 0 |
| stem: degree of zig-zag | slight | absent or very slight |
| stem: anthocyanin coloration of brace roots | strong | absent or very weak |
| stem: anthocyanin coloration of internodes | weak | absent or very weak |
| 4. Plant | | |
| length (tassel included) (only inbred lines and varieties with ear type of grain: sweet or pop) | medium | long |
| ratio height of insertion of peduncle of upper ear to plant | small | medium |

TABLE 3-continued

Physiological and Morphological Characteristics of Sweet Corn Line SEY084-SESM1709

| Characteristic | SEY 084-SESM1709 | Comparison Variety - WE 10 |
|---|---|---|
| length | | |
| peduncle: length | very short | long |
| plant height (to tassel tip) | 89.33 cm standard deviation: 10.8671 sample size: 15 | 91.86 cm standard deviation 7.4712 sample size: 45 |
| ear height (to base of top ear node) | 25.6 cm standard deviation: 3.3094 sample size: 15 | 29.94 cm standard deviation 3.2529 sample size: 45 |
| length of top ear internode | 10.73 cm standard deviation: 0.9611 sample size: 15 | 11.6 cm standard deviation: 1.8103 sample size: 45 |
| average number of tillers | 2.6 avg standard deviation: 0.9102 sample size: 15 | 2.8 avg standard deviation 0.6901 sample size: 45 |
| average number of ears per stalk | 1.7 avg standard deviation: 0.4577 sample size: 15 | 1.46 avg standard deviation: 0.5768 sample size: 45 |
| anthocyanin of brace roots | faint | absent |
| 5. Tassel | | |
| time of anthesis | very early | early |
| anthocyanin coloration at base of glume | strong | absent or very weak |
| anthocyanin coloration of glumes excluding base | strong | absent or very weak |
| anthocyanin coloration of anthers | strong | absent or very weak |
| angle between main axis and lateral branches | large (±75°) | very small |
| curvature of lateral branches | moderately curved | straight |
| number of primary lateral branches | few | medium |
| density of spikelets | moderately lax | medium |
| length of main axis above lowest lateral branch (A-B) | long | medium |
| length of main axis above highest lateral branch (C-D) | very long | short |
| length of lateral branch | medium | medium |
| number of primary lateral branches | 15.6 standard deviation: 2.7723 sample size: 15 | 33.7 standard deviation: 3.9892 sample size: 45 |
| branch angle from central spike | 69.3° standard deviation: 14.3759 sample size: 15 | 34.7° standard deviation: 9.1999 sample size: 45 |
| length (from top leaf collar to tassel tip) | 28.53 cm standard deviation: 1.6417 sample size: 15 | 29.78 cm standard deviation: 3.1981 sample size: 45 |
| pollen shed (0 = male sterile to 9 = heavy shed) | 7 | 8 |
| anther color | 2.5R 6/4 | 2.5GY 8/10 |
| glume color | 2.5R 6/4 | 5GY 6/6 |
| bar glumes (glume bands) | present | absent |
| 6. Ear | | |
| (unhusked data) silk color | 2.5GY 8/4 | 2.5GY 8/6 |
| (unhusked data) fresh husk color | 2.5GY 7/4 | 5GY 6/8 |
| (unhusked data) dry husk color | 2.5Y 8/4 | 2.5Y 8/4 |
| (unhusked data) position of ear at dry husk stage | upright | upright |
| (unhusked data) husk tightness (1 = very loose to 9 = very tight) | 3 | 6 |
| (unhusked data) husk extension (at harvest) | very long (>10 cm) | medium |
| (husked ear data) ear length | 15.74 cm standard deviation: | 15.1 cm standard deviation: |

TABLE 3-continued

Physiological and Morphological Characteristics of Sweet Corn Line SEY084-SESM1709

| Characteristic | SEY 084-SESM1709 | Comparison Variety - WE 10 |
|---|---|---|
| | 1.406 | 2.0126 |
| | sample size: 15 | sample size: 45 |
| (husked ear data) ear diameter at mid-point | 29.94 mm standard deviation: 3.0714 sample size: 15 | 37.02 mm standard deviation: 4.4629 sample size: 45 |
| (husked ear data) ear weight | 24 gm standard deviation: 9.5093 sample size: 15 | 76.8 gm standard deviation: 26.3475 sample size: 45 |
| (husked ear data) number of kernel rows | 6.8 standard deviation: 2.6956 sample size: 15 | 15.8 standard deviation: 3.0608 sample size: 45 |
| (husked ear data) kernel rows | indistinct | distinct |
| (husked ear data) row alignment | slightly curved | straight |
| (husked ear data) shank length | 9.84 cm standard deviation: 2.0992 sample size: 15 | 11.14 cm standard deviation: 3.0598 sample size: 45 |
| (husked ear data) ear taper | extreme | slight |
| length | short | medium |
| diameter (in middle) | small | medium |
| shape | conico-cylindrical | conico-cylindrical |
| number of rows of grain | very few | medium |
| number of colors of grains (only varieties with ear type of grain: sweet or waxy) | one | one |
| grain: intensity of yellow color (only varieties with ear type of grain: sweet) | medium | dark |
| grain: length (only varieties with ear type of grain: sweet) | short | medium |
| grain: width (only varieties with ear type of grain: sweet) | broad | medium |
| type of grain | sweet | sweet |
| shrinkage of top of grain (only varieties with ear type of grain: sweet) | medium | medium |
| color of top of grain | yellow orange | yellow |
| anthocyanin coloration of glumes of cob | absent or very weak | absent |
| time of silk emergence (50% of plants) | very early | late to very late |
| anthocyanin coloration of silks | absent or very weak | absent |
| 8. Cob | | |
| diameter of mid-point | 21.5 mm standard deviation: 1.3512 sample size: 15 | 27.65 mm standard deviation: 2.1848 sample size: 45 |
| color | 5Y 8/4 | 2.5Y 8/4 |
| 9. Kernel (dried) | | |
| length | 7.38 mm standard deviation: 1.6234 sample size: 15 | 7.05 mm standard deviation: 0.9999 sample size: 45 |
| width | 9.48 mm standard deviation: 0.6885 sample size: 15 | 6.75 mm standard deviation: 0.8364 sample size: 45 |
| thickness | 4.56 mm standard deviation: 0.7393 sample size: 15 | 5 mm standard deviation 0.9935 sample size: 45 |
| % round kernels (shape grade) | sample size: 15 | sample size: 45 |
| aleurone color pattern | homozygous | homozygous |
| aleurone color | 5Y 8/12 | 2.5Y 8/10 |
| hard endosperm color | 5Y 8/12 | 2.5Y 8/10 |
| endosperm type | sweet (su1) | sweet |
| weight per 100 kernels (unsized sample) | 22 gm sample size: 100 | 16.25 gm sample size: 200 |

TABLE 3-continued

Physiological and Morphological Characteristics of Sweet Corn Line SEY084-SESM1709

| Characteristic | SEY 084-SESM1709 | Comparison Variety - WE 10 |
|---|---|---|
| 10. Agronomic Traits | | |
| stay green (at 65 days after anthesis) (from 1 = worst to 9 = excellent) | 1 | 7 |

*These are typical values. Values may vary due to environment. Other values that are substantially equivalent are also within the scope of the invention.

C. Breeding Corn Plants

One aspect of the current invention concerns methods for producing seed of sweet corn hybrid SEY6RH1263 involving crossing sweet corn lines SEY-6RNTB001 and SEY084-SESM1709. Alternatively, in other embodiments of the invention, hybrid SEY6RH1263, line SEY-6RNTB001, or line SEY084-SESM1709 may be crossed with itself or with any second plant. Such methods can be used for propagation of hybrid SEY6RH1263 and/or the sweet corn lines SEY-6RNTB001 and SEY084-SESM1709, or can be used to produce plants that are derived from hybrid SEY6RH1263 and/or the sweet corn lines SEY-6RNTB001 and SEY084-SESM1709. Plants derived from hybrid SEY6RH1263 and/or the sweet corn lines SEY-6RNTB001 and SEY084-SESM1709 may be used, in certain embodiments, for the development of new corn varieties.

The development of new varieties using one or more starting varieties is well known in the art. In accordance with the invention, novel varieties may be created by crossing hybrid SEY6RH1263 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.\

The plants of the present invention are particularly well suited for the development of new lines based on the elite nature of the genetic background of the plants. In selecting a second plant to cross with SEY6RH1263 and/or sweet corn lines SEY-6RNTB001 and SEY084-SESM1709 for the purpose of developing novel corn lines, it will typically be preferred to choose those plants which either themselves exhibit one or more selected desirable characteristics or which exhibit the desired characteristic(s) when in hybrid combination. Examples of desirable traits may include, in specific embodiments, male sterility, herbicide resistance, resistance for bacterial, fungal, or viral disease, insect resistance, male fertility, sugar content, and enhanced nutritional quality.

D. Performance Characteristics

As described above, hybrid SEY6RH1263 exhibits desirable agronomic traits. The performance characteristics of hybrid SEY6RH1263 were the subject of an objective analysis of the performance traits relative to other varieties. The results of the analysis are presented below.

TABLE 4

Performance Data for Hybrid SEY6RH1263

| hybrid | % Moisture | % recovery | Green Ear wt tons/acre | Cases cut corn/acre (@ 14.25 lbs/case) | Cases cut corn/ton green ear | Avg Ear Length | Avg Ear Diameter | Kernel Row Number |
|---|---|---|---|---|---|---|---|---|
| SEY6RH1263 Average | 70.1 | 60.0 | 9.3 | 781 | 84 | 8.38 | 2.20 | 18 |
| GH 2042 Average | 68.1 | 50.1 | 8.7 | 613 | 70 | 8.02 | 2.00 | 17.2 |
| GH 4927 Average | 68.1 | 46.9 | 7.9 | 521 | 66 | 8.11 | 1.97 | 17.4 |

2010 Early Sugary Yellow Processor Sweet Corn Yield Trial - Adams, WI.

TABLE 5

Additional Performance Data for Hybrid SEY6RH1263

| DESC | Heat Units to Harvest | Harvest Moistue % | Green ear Wt. (lbs/Acre) | Cases cut kernels/ acre (14.25 lbs/ case) | % Recovery |
|---|---|---|---|---|---|
| GH4927 | 1695 | 71.8 | 19,700 | 379.5 | 27.5 |
| SEY6RH1263 | 1704 | 75.0 | 19,200 | 510.6 | 39.4 |
| This record contains LSDs for each trait | 31 | 1.7 | 3,000 | 79.2 | 5.8 |

2010 South Central Minnesota Sugary Yellow Hybrid Yield Trial. 2 planting dates with 3 reps per planting.

E. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those corn plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental corn plant which contributes the locus for the desired characteristic is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a corn plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny corn plants of a backcross in which a plant described herein is the recurrent parent comprise (i) the desired trait from the non-recurrent parent and (ii) all of the physiological and morphological characteristics of corn the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, waxy starch, herbicide resistance, resistance for bacterial, fungal, or viral disease, insect resistance, sugar content, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of corn plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., 1985), including in monocots (see, e.g., Dekeyser et al., 1990; Terada and Shimamoto, 1990); a tandemly duplicated version of the CaMV 35S promoter, the enhanced 35S promoter (P-e35S); 1 the nopaline synthase promoter (An et al., 1988); the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a corn plant according to the invention. Non-limiting examples of particular genes and corresponding phenotypes one may choose to introduce into a corn plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a corn variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a corn plant by transformation.

H. Deposit Information

A deposit of sweet corn hybrid SEY6RH1263 and inbred parent line SEY-6RNTB001, disclosed above and recited in the claims, has been made with the American Type Culture Collection (ATCC), 10801 University Blvd., Manassas, Va. 20110-2209. The date of the deposits were Apr. 22, 2011 and Apr. 13, 2011, respectively. The accession numbers for those deposited seeds of sweet corn hybrid SEY6RH1263 and inbred parent line SEY-6RNTB001 are ATCC Accession Number PTA-11845 and ATCC Accession Number PTA-11815, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A corn plant comprising at least a first set of the chromosomes of sweet corn line SEY-6RNTB001, a sample of seed of said line having been deposited under ATCC Accession No. PTA-11815.

2. A seed comprising at least a first set of the chromosomes of sweet corn line SEY-6RNTB001, a sample of seed of said line having been deposited under ATCC Accession No. PTA-11815.

3. The plant of claim 1, which is hybrid.

4. The plant of claim 3, wherein the hybrid plant is sweet corn hybrid SEY6RH1263, a sample of seed of said hybrid having been deposited under ATCC Accession No. PTA-11845.

5. A plant part of the plant of claim 1.

6. The plant part of claim 5, further defined as an ear, ovule, pollen or cell.

7. The plant part of claim 6, further defined as a cell.

8. A corn plant, or a part thereof, having all the physiological and morphological characteristics of the corn plant of claim 1.

9. A corn plant, or a part thereof, having all the physiological and morphological characteristics of the corn plant of claim 4.

10. A tissue culture of regenerable cells of the plant of claim 1.

11. The tissue culture according to claim 10, comprising cells or protoplasts from a plant part selected from the group consisting of leaf, pollen, embryo, root, root tip, anther, silk, flower, kernel, ear, cob, husk, stalk and meristem.

12. A corn plant regenerated from the tissue culture of claim 11.

13. A method of vegetatively propagating the plant of claim 1 comprising the steps of:
    (a) obtaining tissue capable of being propagated from a plant according to claim 1;
    (b) cultivating said tissue to obtain proliferated shoots; and
    (c) rooting said proliferated shoots to obtain rooted plantlets.

14. A method of introducing a desired trait into a corn line comprising:
    (a) crossing a plant of line SEY-6RNTB001, a sample of seed of said line having been deposited under ATCC Accession No. PTA-11815, with a second corn plant that comprises a desired trait to produce F1 progeny;
    (b) selecting an F1 progeny that comprises the desired trait;
    (c) crossing the selected F1 progeny with a plant of line SEY-6RNTB001 to produce backcross progeny; and
    (d) repeating steps (b) and (c) three or more times to produce selected fourth or higher backcross progeny that comprise the desired trait.

15. A corn plant produced by the method of claim 14.

16. A method of producing a plant comprising a transgene, the method comprising introducing a transgene into a plant of sweet corn hybrid SEY6RH1263 or sweet corn line SEY-6RNTB001, a sample of seed of said hybrid and line having been deposited under ATCC Accession No. PTA-11845 and ATCC Accession No. PTA-11815, respectively.

17. A plant produced by the method of claim 16.

18. A plant of sweet corn hybrid SEY6RH1263 or sweet corn line SEY-6RNTB001 further comprising a transgene, a sample of seed of said hybrid and line having been deposited under ATCC Accession No. PTA-11845 and ATCC Accession No. PTA-11815, respectively.

19. A seed that produces the plant of claim 18.

20. A plant of sweet corn hybrid SEY6RH1263 or sweet corn line SEY-6RNTB001 comprising a single locus conversion, a sample of seed of said hybrid and line having been deposited under ATCC Accession No. PTA-11845 and ATCC Accession No. PTA-11815, respectively.

21. A seed that produces the plant of claim 20.

22. A method for producing a seed of a plant derived from hybrid SEY6RH1263 or line SEY-6RNTB001 comprising the steps of:
    (a) crossing a corn plant of hybrid SEY6RH1263 or line SEY-6RNTB001 with a second corn plant; a sample of seed of said hybrid and line having been deposited under ATCC Accession No. PTA-11845 and ATCC Accession No. PTA-11815, respectively; and
    (b) allowing seed of a hybrid SEY6RH1263 or line SEY-6RNT8001-derived corn plant to form.

23. The method of claim 22, further comprising the steps of:
    (c) crossing a plant grown from said hybrid SEY6RH1263 or SEY-6RNTB001-derived sweet corn seed with itself or a second sweet corn plant to yield additional hybrid SEY6RH1263 or SEY-6RNTB001-derived corn seed;
(d) growing said additional hybrid SEY6RH1263 or SEY-6RNTB001-derived corn seed of step (c) to yield additional hybrid SEY6RH1263 or SEY-6RNTB001-derived corn plants; and
(e) repeating the crossing and growing steps of (c) and (d) to generate at least a first further hybrid SEY6RH 1263 or SEY-6RNTB001-derived corn plant.

24. The method of claim 22, wherein the second corn plant is of an inbred corn line.

25. A method of producing a corn comprising:
(a) obtaining a plant according to claim 1, wherein the plant has been cultivated to maturity; and
(b) collecting a corn from the plant.

26. The method of claim 25, wherein the plant is a plant of sweet corn hybrid SEY6RH1263, a sample of seed of said hybrid SEY6RH1263 having been deposited under ATCC Accession No. PTA-11845.

27. A method of producing seed comprising crossing the plant of claim 1 with itself or a second plant.

* * * * *